United States Patent
Scholten

(10) Patent No.: US 9,468,522 B2
(45) Date of Patent: Oct. 18, 2016

(54) IMPLANT DEVICE, SENSOR MODULE, SINGLE-USE INJECTOR AND METHOD FOR PRODUCING AN IMPLANT DEVICE

(71) Applicant: IMPLANDATA OPHTHALMIC PRODUCTS GMBH, Hannover (DE)

(72) Inventor: Dick Scholten, Stuttgart (DE)

(73) Assignee: Implandata Ophthalmic Products GmbH, Hannover (DE)

( * ) Notice: Subject to any disclaimer, the term of this patent is extended or adjusted under 35 U.S.C. 154(b) by 0 days.

(21) Appl. No.: 14/372,264

(22) PCT Filed: Jan. 10, 2013

(86) PCT No.: PCT/EP2013/050334
§ 371 (c)(1),
(2) Date: Jul. 15, 2014

(87) PCT Pub. No.: WO2013/107677
PCT Pub. Date: Jul. 25, 2013

(65) Prior Publication Data
US 2015/0094806 A1    Apr. 2, 2015

(30) Foreign Application Priority Data
Jan. 17, 2012    (DE) .................. 10 2012 200 574

(51) Int. Cl.
*A61F 2/16* (2006.01)
*A61B 3/16* (2006.01)
*A61F 9/00* (2006.01)

(52) U.S. Cl.
CPC . *A61F 2/16* (2013.01); *A61B 3/16* (2013.01); *A61F 2/1613* (2013.01); *A61F 2/1662* (2013.01); *A61F 2/1694* (2013.01); *A61F 9/0017* (2013.01); *A61F 2002/1699* (2015.04); *A61F 2220/0008* (2013.01); *A61F 2220/0025* (2013.01); *A61F 2220/0091* (2013.01); *A61F 2240/001* (2013.01); *Y10T 29/49002* (2015.01)

(58) Field of Classification Search
CPC ...... A61F 2/16; A61F 2/1613; A61F 2/1694; A61B 5/03; A61B 3/16
See application file for complete search history.

(56) References Cited

U.S. PATENT DOCUMENTS 5,005,577 A    4/1991    Frenkel

FOREIGN PATENT DOCUMENTS

| EP | 0512785 | 11/1992 |
|---|---|---|
| WO | WO 01/21063 | 3/2001 |
| WO | WO 2007/127305 | 11/2007 |

OTHER PUBLICATIONS

Eggers, T., et al., "Wireless Eye Pressure Monitoring System Integrated into Intra-Ocular Lens", Proc. Micro. Tec. VDE World Microtech. Congress, Sep. 25, 2000, pp. 255-258.

*Primary Examiner* — Howie Matthews
(74) *Attorney, Agent, or Firm* — Notaro, Michalos & Zaccaria P.C.

(57) ABSTRACT

The invention relates to an implant device comprising a sensor module which comprises one or more first fastening means, an implant module which comprises one or more second fastening means, and a connecting module, by means of which the sensor module is connected to the implant module via the one or the first fastening means and via the one or the second fastening means, and comprising a fold axis, along which the implant device can be folded up.

17 Claims, 6 Drawing Sheets

IMPLANT DEVICE, SENSOR MODULE, SINGLE-USE INJECTOR AND METHOD FOR PRODUCING AN IMPLANT DEVICE

The invention relates to an implant device, to a sensor module, to a single-use injector and to a method for producing an implant device.

PRIOR ART

Glaucoma is one of the most frequent disorders of the optic nerve, and is characterised by a continuous loss of nerve fibres, which may lead to scotomas and, in extreme cases, to loss of sight in the eye. The most significant risk factor is considered to be an excessively high intraocular pressure.

For optimal treatment, it is necessary to precisely monitor the progression of the disease and the risk factors, such as the intraocular pressure. Intraocular pressure means the physical pressure which is being exerted on the inner wall of the eye. It causes a constantly smooth curvature of the surface of the cornea and a constant distance between the cornea, the lens and the retina of the eye, and an even alignment of the photo receptors on the retina. In addition, the intraocular pressure maintains the stable spherical shape of the eyeball. Medical practice uses appropriate measuring apparatuses for determining intraocular pressure.

If the intraocular pressure exceeds certain limit values for certain periods of time, the intracellular transport within the nerve fibres can be impaired such that the nerve fibres die.

Since, above all, the intraocular pressure may vary extremely greatly, it is necessary for this to be frequently measured in order to achieve an accurate diagnosis. The most direct measurement would be a measurement which takes place directly in the eye. Ideally, the aim is to avoid an implant; however, every year an extremely large number of intraocular lenses are implanted: in 2007 alone, 600,000 were implanted in Germany.

WO 2001 021 063 A1 describes a device for measuring physical variables in the eye, more particularly the intraocular pressure, comprising a telemetry system which comprises a pressure sensor integrated into the intraocular lens. When producing the device described therein, the pressure sensor is encapsulated and the intraocular lens is formed at the same time in a silicone moulding process. In this process, an incision in the eye of usually more than 3 mm is required to implant such an intraocular lens. In addition, owing to the process, only silicone can be used as a lens material because other materials cannot be used in a silicone moulding process. Owing to the rigid mechanical connection between the pressure sensor module and the intraocular lens, it is possible for the pressure sensor module to deform, thereby distorting the optical imaging of the intraocular lens.

DISCLOSURE OF THE INVENTION

According to one aspect, the present invention provides an implant device comprising a sensor module which comprises one or more first fastening means, an implant module which comprises one or more second fastening means, and a connecting module, by means of which the sensor module is connected to the implant module via the one or the first fastening means and via the one or the second fastening means, and comprising a fold axis, along which the implant device can be folded up.

According to a further aspect, the present invention provides a sensor module comprising one or more first fastening means which are designed to fix a connecting module, and at least one fold axis, along which the sensor module can be folded up.

According to a further aspect, the present invention provides a single-use injector comprising an implant device.

According to a further aspect, the present invention provides a method for producing an implant device.

Advantages of the Invention

One concept of the present invention is to provide a foldable connection between the sensor module and the intraocular lens.

In particular, the connections between the sensor module and the intraocular lens are intended to be flexible. As a result, shifts of the sensor module are less critical for the intraocular lens. Advantageously, the flexible connection also allows the intraocular lens and the sensor module to be implanted successively. A smaller incision length in the eye is thus necessary, particularly when using foldable sensor modules. In addition, when using a non-monolithic, flexible connection, it is possible to use other lens materials, such as poly(methyl methacrylate) (PMMA), commonly referred to as acrylic glass or Plexiglas, or hydrogels, that is to say water-containing but water-insoluble polymers, the molecules of which are chemically linked by covalent or ionic bonds or are physically linked by entangling the polymer chains to form a three-dimensional network.

For optimal optical imaging, the intraocular lens has to be positioned and fixed in the correct position in the eye. The intraocular lens can then function as a frame on which the sensor module can be unfolded and positioned.

According to an embodiment of the invention, the implant module is formed as an intraocular lens.

According to a further embodiment of the invention, the implant module is formed as a capsule clamping ring.

According to a further embodiment of the invention, the sensor module is formed as a pressure sensor module.

According to a further embodiment of the invention, the one or more first fastening means of the sensor module are formed as eyelets.

According to a further embodiment of the invention, the one or more second fastening means of the implant module are formed as eyelets.

According to a further embodiment of the invention, the implant device is provided for use in an injector or an injector set, by means of which the implant device is intended to be implanted.

The above-described configurations and developments can, where appropriate, be combined with one another in any way.

Further possible configurations, developments and implementations of the invention also include combinations, which are not explicitly mentioned, of features of the invention which are previously described or are described in the following with reference to the embodiments.

BRIEF DESCRIPTION OF THE DRAWINGS

The accompanying drawings are intended to provide a better understanding of the embodiments of the invention. Said drawings show embodiments and are used in conjunction with the description to explain principles and concepts of the invention.

Other embodiments and many of the above-mentioned advantages emerge on the basis of the drawings. The elements shown in the drawings are not necessarily to scale.

In the drawings:

DESCRIPTION OF THE PREFERRED EMBODIMENT

Figure 1:
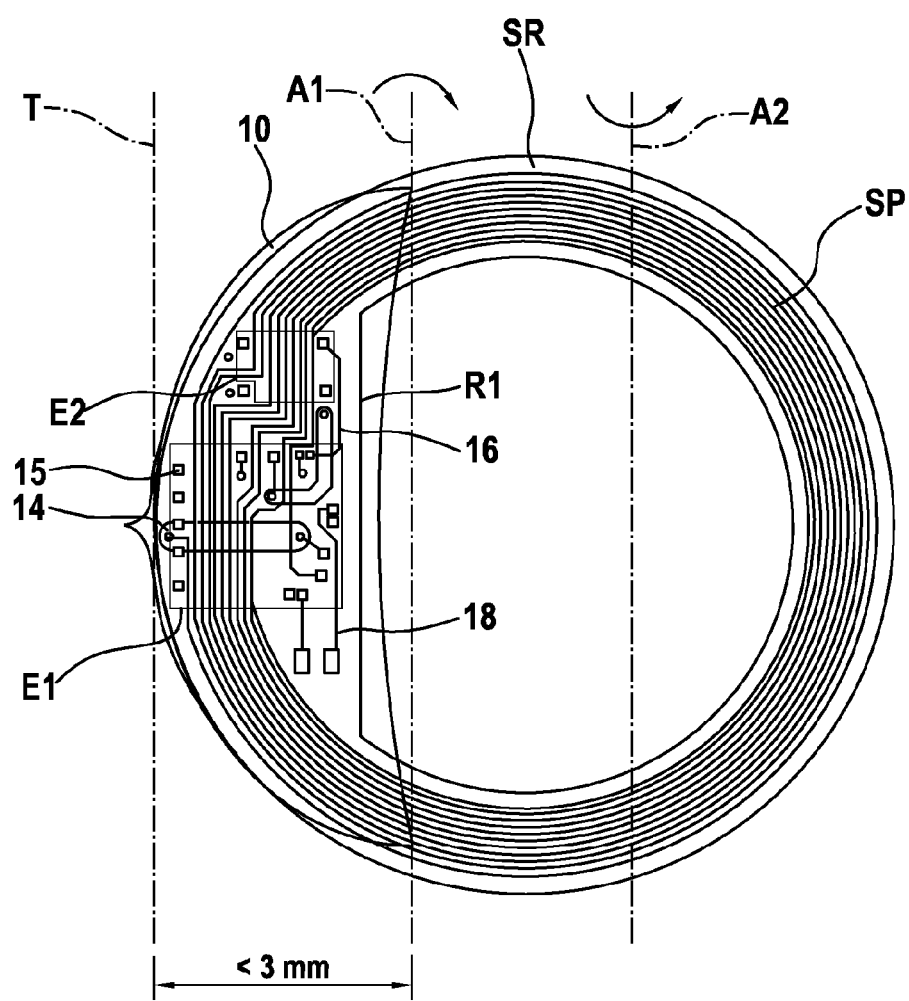
Figure 2:
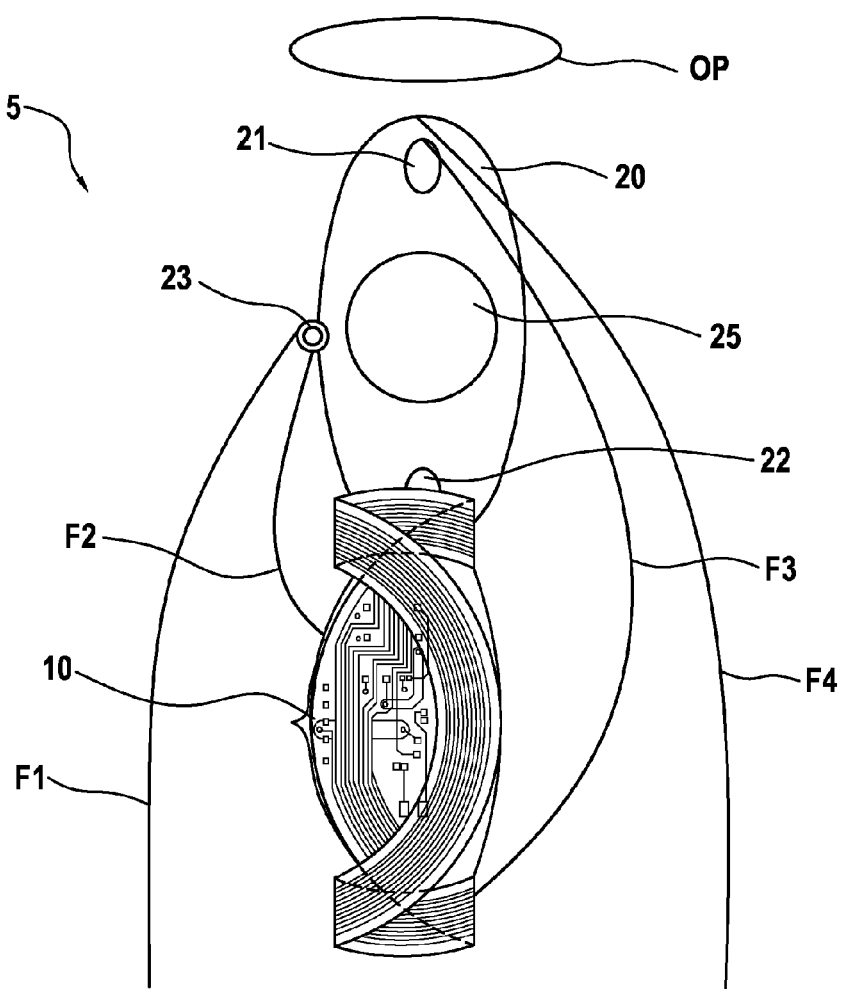
Figure 3:
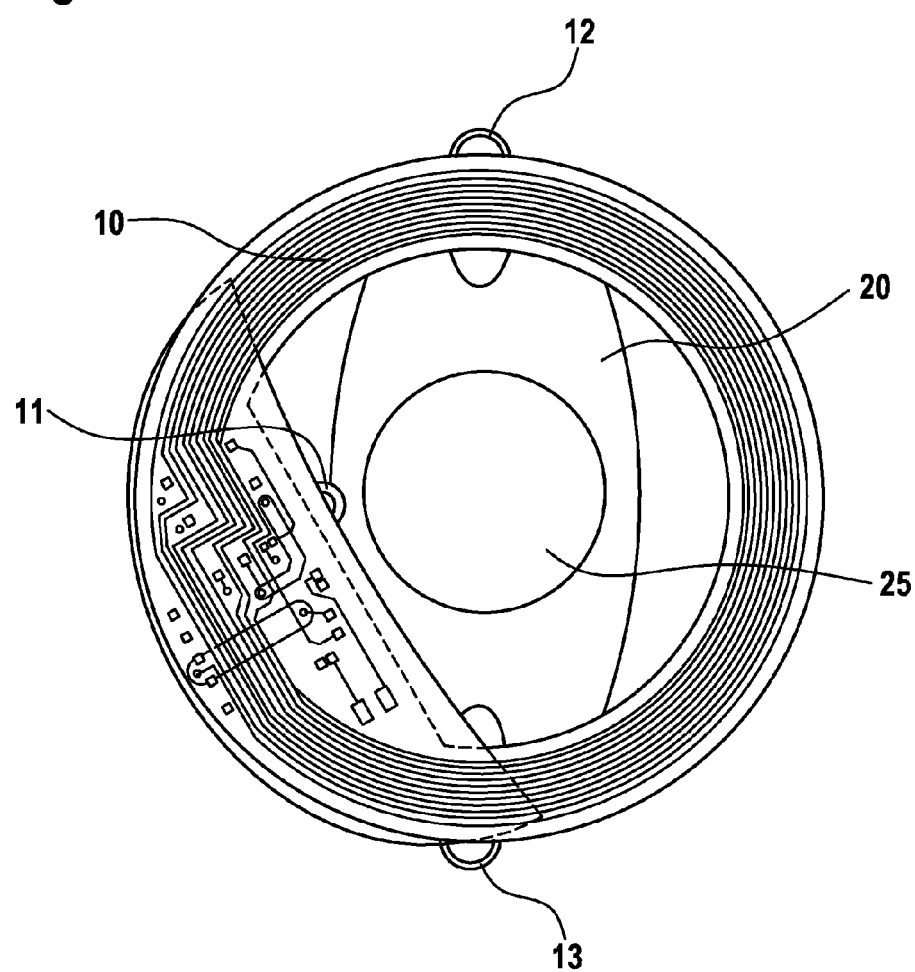
Figure 6:
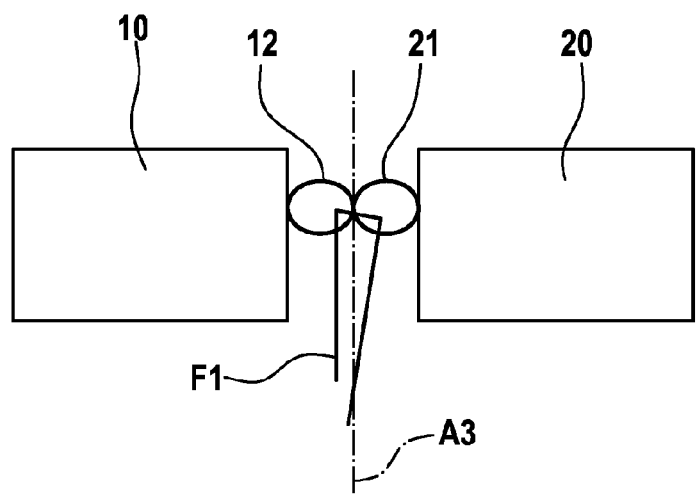
Figure 7:
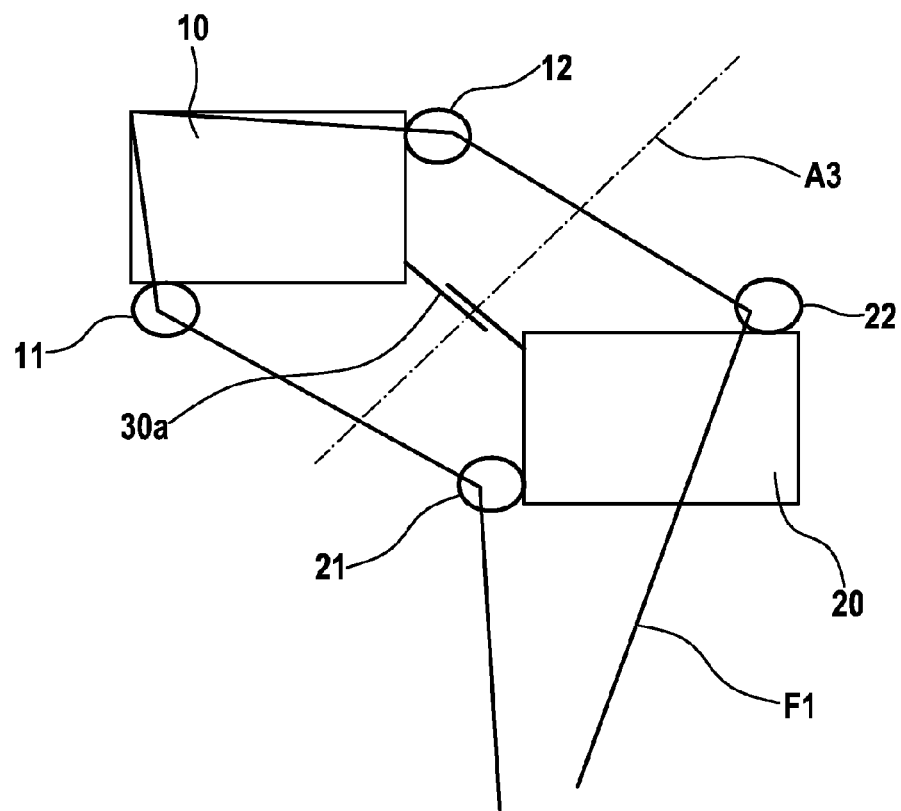
Figure 8:
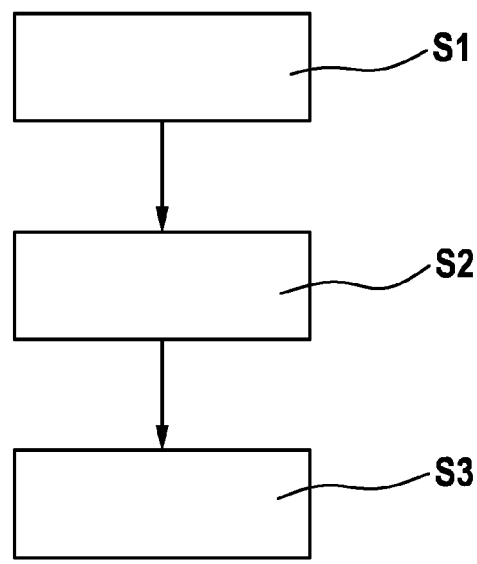

FIG. 1 is a schematic view of a sensor module according to an embodiment of the invention;

FIG. 2 is a schematic view of an implant device before it is guided through an operation opening according to a further embodiment of the invention;

FIG. 3 is a schematic view of an implant device after it is guided through an operation opening according to a further embodiment of the invention;

FIG. 4-7 are each schematic views of an implant device according to a further embodiment of the invention; and FIG. 8 schematically shows a flow diagram of the method for producing an implant device according to a further embodiment of the invention.

In the figures of the drawings, like reference numerals denote like or functionally like elements, parts, components or method steps, unless stated otherwise.

FIG. 1 is a schematic view of a sensor module according to an embodiment of the invention.

A sensor module 10 comprises one or more folding axes A1, A2 along which the sensor module can be folded up. For example, the folding axes A1, A2 are parallel to a tangent T of the sensor module 10.

The sensor module 10 is integrated onto a foldable carrier SR and further comprises a coil SP integrated into the foldable carrier SR, which for example is formed in a planar manner in a flat surface in the form of a plurality of coil windings which are positioned side by side.

The electronics of the sensor module 10 is integrated for example into switching means E1, E2 which comprise flexible strip conductors 14, 15, 16, 18 and additional components. The electronics can be integrated into a single electronics carrier R1.

The sensor module 10 is coated for example with parylene or another inert polymer coating material.

FIG. 2 is a schematic view of an implant device before it is guided through an operation opening OP according to a further embodiment of the invention.

An implant device 5 comprises a sensor module 10 and an implant module 20. The implant module 20 comprises one or more second fastening elements 21, 22, 23.

For example, the fastening elements 21, 22, 23 are formed to receive threads F1-F4. Advantageously, the fastening elements 21, 22, 23 are formed as eyelets or as another fastening element from a ring made of a biocompatible plastics material or metal.

By means of the threads F1-F4, the implant device 5 can be unfolded after being pushed through the operation opening OP. The implant device 5 can thus be unfolded again in its final position inside the body by a tensile force applied via the threads F1-F4.

For this purpose, the implant module is for example held in place using tweezers and at the same time a tensile force is applied to the threads F1 and/or F4.

The implant module 20 is coated for example with parylene or another inert polymer coating material.

The implant module 20 is formed as, for example, an intraocular lens or as another artificial lens which is to be implanted into the eye, and said module comprises a lens 25. The coil SP and the associated carrier SR of the sensor module 10 of the implant device 5 are arranged concentrically with the lens 25 of the implant module 20 in this case.

FIG. 3 is a schematic view of an implant device after it is guided through an operation opening according to a further embodiment of the invention.

The implant device 5 comprises the sensor module 10 and the implant module 20. The sensor module 10 comprises one or more first fastening means 11, 12, 13, which are designed to fix a connecting module 30.

FIGS. 4 to 7 are each schematic views of an implant device according to a further embodiment of the invention.

The additional reference numerals used in FIG. 3 are already described in the figure description associated with FIG. 2 and are therefore not explained in any further detail.

Figure 4:
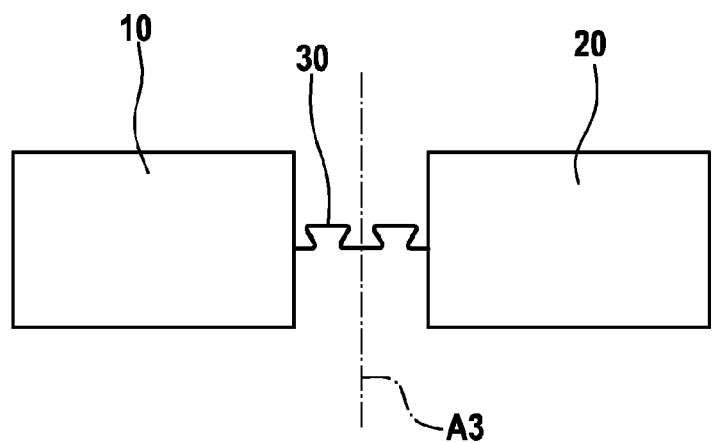

FIG. 4 shows an implant device 5 comprising a flexible connecting module 30. The connecting module 30 shown in FIG. 4 is made of a flexible or foldable material, for example. Owing to the use of the flexible connecting module 30, the implant device 5 has a fold axis A3, along which the implant device 5 can be folded up.

The additional reference numerals used in FIG. 4 are already described in the figure description associated with FIG. 2 and are therefore not explained in any further detail.

Figure 5:
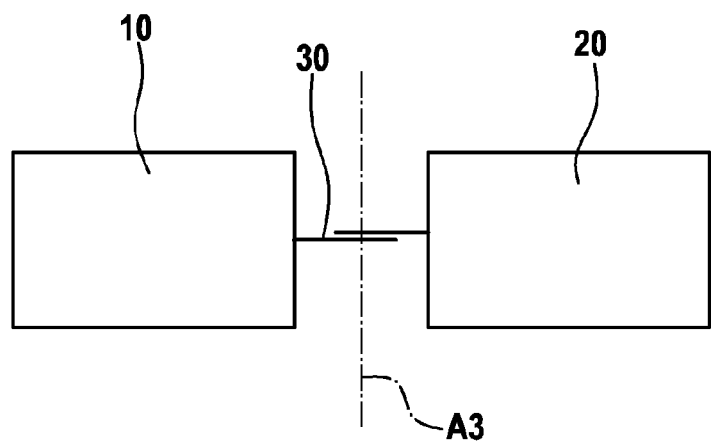

The connecting module 30 shown in FIG. 5 is formed for example as a flexible hinge part. By means of the hinge part, the implant device 5 has a fold axis A3, along which the implant device 5 can be folded up.

The additional reference numerals used in FIG. 5 are already described in the figure description associated with FIG. 2 and are therefore not explained in any further detail.

The implant device 5 shown in FIG. 6 comprises a connecting module 30, which is formed for example by a thread F1 and a first fastening means 12 of the sensor module 10 and second fastening means 21 of the implant module 20.

The additional reference numerals used in FIG. 6 are already described in the figure description associated with FIG. 2 and are therefore not explained in any further detail.

The connecting module 30 shown in FIG. 7 is formed for example on one hand by a hinge part 30a and on the other hand by a thread F1 and two first fastening means 11, 12 of the sensor module 10 and two second fastening means 21, 22 of the implant module 20.

The additional reference numerals used in FIG. 7 are already described in the figure description associated with FIG. 2 and are therefore not explained in any further detail.

FIG. 8 schematically shows a flow diagram of the method for producing an implant device according to a further embodiment of the invention.

The method for producing an implant device includes the following method steps.

As a first method step, a sensor module 10, an implant module 20 and a connecting module 30 are provided S1.

As a second method step, the sensor module 10, the implant module 20 and the connecting module 30 are assembled S2 to form the implant device 5, the threads F1-F4, for example, being pulled through the first fastening means 11-13, formed as eyelets, or through the second fastening means 21-23, formed as eyelets, of the sensor module 10 and of the implant module 20 respectively.

As a third method step, the assembled implant device 5 is folded S3 along a fold axis A3 of the implant device 5 for folding up the implant device 5.

The invention claimed is:

1. Implant device comprising:
a sensor module (10) which comprises one or more first fastening means (11-13);
an implant module (20) in the form of an intraocular lens (25) and comprising one or more second fastening means (21-23); and
a connecting module (30), by means of which the sensor module (10) is connected to the implant module (20) via the one or the first fastening means (11-13) and via the one or the second fastening means (21-23); and
a fold axis (A3), along which the implant device can be folded up at the connection module (30) between an unfolded condition before implanting and a folded condition after implanting.

2. Implant device according to claim 1, wherein the sensor module (10) is formed as a pressure sensor module.

3. Implant device according to claim 1, wherein the one or more first fastening means (11-13) of the sensor module (10) are formed as eyelets.

4. Implant device according to claim 1, wherein the one or more second fastening means (21-23) of the implant module (20) are formed as eyelets.

5. Implant device according to claim 1, wherein the connecting module (30) is formed as a hinge part or as a flexible or foldable material.

6. Implant device according to claim 1, wherein the sensor module (10) and the implant module (20) are also flexibly connected by means of one or more threads (F1-F4) via the connecting module (30).

7. Implant device according to claim 6, wherein the one or more threads (F1-F4) are fixed by knotting or by bonding or by clamping the one or more threads (F1-F4).

8. Implant device according to claim 6, wherein the one or more threads (F1-F4) are surgical threads.

9. Implant device according to claim 1, wherein the implant device (5) is provided for use in an injector or an injector set, by means of which the implant device (5) is intended to be implanted.

10. An implant device comprising:
a sensor module (10) which comprises one or more first fastening means (11-13);
an implant module (20) in the form of an intraocular lens (25) and comprising one or more second fastening means (21-23); and
a connecting module (30), by means of which the sensor module (10) is connected to the implant module (20) via the one or the first fastening means (11-13) and via the one or the second fastening means (21-23);
a fold axis (A3), along which the implant device can be folded up at the connection module (30) between an unfolded condition before implanting and a folded condition after implanting;
the sensor module (10) and the implant module (20) being flexibly connected by means of one or more threads (F1-F4) via the connecting module (30).

11. The implant device according to claim 10, wherein the sensor module (10) is formed as a pressure sensor module.

12. The implant device according to claim 10, wherein the one or more first fastening means (11-13) of the sensor module (10) are formed as eyelets.

13. The implant device according to claim 10, wherein the one or more second fastening means (21-23) of the implant module (20) are formed as eyelets.

14. The implant device according to claim 10, wherein the connecting module (30) is formed as a hinge part or as a flexible or foldable material.

15. The implant device according to claim 10, wherein the one or more threads (F1-F4) are fixed by knotting or by bonding or by clamping the one or more threads (F1-F4).

16. The implant device according to claim 10, wherein the one or more threads (F1-F4) are surgical threads.

17. The implant device according to claim 10, wherein the implant device (5) is provided for use in an injector or an injector set, by means of which the implant device (5) is intended to be implanted.

* * * * *